US008524252B2

(12) United States Patent
Youil et al.

(10) Patent No.: US 8,524,252 B2
(45) Date of Patent: Sep. 3, 2013

(54) **TEMPERATURE SENSITIVE VACCINE STRAIN OF *MYCOPLASMA HYOPNEUMONIAE* AND USES THEREOF**

(75) Inventors: Rima Youil, Port Melbourne (AU); Youssef Abs El-Osta, Glenroy (AU); Glenn Browning, Victoria (AU); Phillip Markham, Victoria (AU)

(73) Assignees: Bioproperties Pty Ltd. (AU); The University of Melbourne (AU)

( * ) Notice: Subject to any disclaimer, the term of this patent is extended or adjusted under 35 U.S.C. 154(b) by 0 days.

(21) Appl. No.: 13/321,662

(22) PCT Filed: May 19, 2010

(86) PCT No.: PCT/AU2010/000590
§ 371 (c)(1),
(2), (4) Date: Feb. 13, 2012

(87) PCT Pub. No.: WO2010/132932
PCT Pub. Date: Nov. 25, 2010

(65) Prior Publication Data
US 2012/0135040 A1 May 31, 2012

(30) Foreign Application Priority Data
May 19, 2009 (AU) ................................ 2009902255

(51) Int. Cl.
*A61K 39/02* (2006.01)
(52) U.S. Cl.
USPC ..................................... 424/264.1; 435/252.3
(58) Field of Classification Search
None
See application file for complete search history.

(56) References Cited

U.S. PATENT DOCUMENTS

| | | | | |
|---|---|---|---|---|
| 6,585,981 | B1 * | 7/2003 | Pijoan | 424/264.1 |
| 6,673,567 | B2 * | 1/2004 | Sharpe et al. | 435/29 |
| 2003/0092897 | A1 * | 5/2003 | Walker et al. | 536/23.1 |
| 2006/0233831 | A1 * | 10/2006 | Parisot et al. | 424/204.1 |
| 2009/0117152 | A1 * | 5/2009 | Chu et al. | 424/201.1 |
| 2011/0129494 | A1 * | 6/2011 | Detraz et al. | 424/204.1 |

FOREIGN PATENT DOCUMENTS
WO   WO 02/10343   2/2002

OTHER PUBLICATIONS

Mayor, Desiree, et al, Veterinary Research, vol. 38, 2007, pp. 391-398, Diversity of *Mycoplasma hyopneumoniae* in pig farms revealed by direct molecular typing of clinical material.*
Hsu, Tsungda et al, Infection and Immunity, vol. 66(10), pp. 4762-4766, Oct. 1998, Identification of the cilum binding epitope of the *Mycoplasma hyopneumoniae* P97 Adhesin.*
Blanchard, Beatrice et al, Microbiology, vol. 142, pates 1855-'862, 1996, Analysis of putative ABC transporter genes in *Mycoplasma hyopneumoniae*.*
Schmidt, Jonathan A et al, Journal of Bacterilogy, 2007, vol. 189(9), pp. 3414-3424, *Mycoplasma hyopneumoniae* mhp379 is a Ca2+ Dependent, sugar-nonspecific exonuclease exposed on the cell surface.*
PCT/AU2010/000590 International Search Report dated Jul. 14, 2010 (4 pages).

* cited by examiner

*Primary Examiner* — Albert Navarro
*Assistant Examiner* — Ginny Portner
(74) *Attorney, Agent, or Firm* — Brinks Hofer Gilson & Lione

(57) ABSTRACT

The present invention relates to a *Mycoplasma hyopneumoniae* vaccine strain comprising a mutation in at least one of the genes listed or as deposited with the National Measurements Institute (Australia) under accession number NM04/41259, which strain is temperature sensitive and attenuated, a vaccine comprising such strains and methods and uses thereof.

19 Claims, 6 Drawing Sheets

Protective Index (severity of lung lesions)

TEMPERATURE SENSITIVE VACCINE STRAIN OF *MYCOPLASMA HYOPNEUMONIAE* AND USES THEREOF

FIELD

The present invention relates to *Mycoplasma hyopneumoniae* strains, vaccines comprising such strains and uses of such vaccines for protecting against mycoplasmal pneumonia in swine.

BACKGROUND

*Mycoplasma hyopneumoniae* is the etiological agent of swine mycoplasmal pneumonia (also called enzootic pneumonia (EP)). It is one of the most common and economically significant respiratory diseases affecting swine production worldwide. The disease is associated with secondary infections, high-morbidity and low-mortality rates, low feed conversion and can be attributed to global economic losses estimated at about $1 billion per year.

In EP, *Mycoplasma hyopneumoniae* bacteria attach to the cilia of epithelial cells in the lungs of swine destroying healthy normal cilia allowing for opportunistic organisms to establish themselves into the respiratory tissue causing disease. Once established, *M. hyopneumoniae* causes lesions in the lungs of pigs.

The disease is highly contagious and transmission is usually through direct contact with infected respiratory tract secretions, for example droplets ejected from the snout or mouth on sneezing or coughing.

Several vaccines against *M. hyopneumoniae* currently exist. Most current vaccines are provided by about 10 companies with 22 vaccine brands registered as either single or bi/multivalent. All are killed or inactivated *M. hyopneumoniae* preparations.

Examples of whole cell inactivated *M. hyopneumoniae* vaccines include RESPISURE™ and STELLAMUNE™ (Pfizer), SUVAXYN M. HYO™ (Fort Dodge), HYORESP™ (Meriel), M+PAC™ (Schering-Plough) and PORCILIS™ (Intervet).

While some vaccines can reduce the severity of EP, none of the available whole cell killed or inactivated vaccines provide full protection from *M. hyopneumoniae* infection. Accordingly there is a need for a more effective vaccine.

It is an aim of a preferred embodiment of the present invention to provide a live strain of *Mycoplasma pneumoniae* suitable for use in vaccination to prevent enzootic pneumonia.

All references, including any patents or patent applications, cited in this specification are hereby incorporated by reference. It will be clearly understood that, although a number of prior art publications are referred to herein, this reference does not constitute an admission that any of these documents forms part of the common general knowledge in the art.

SUMMARY

The invention generally provides a live attenuated *Mycoplasma hyopneumoniae* strain that can be used to produce a live vaccine that is effective in protecting against enzootic pneumonia in pigs.

A first aspect provides an attenuated *Mycoplasma hyopneumoniae* vaccine strain comprising a mutation in at least one of the genes listed in Table 1.

In one embodiment the vaccine strain comprises a mutation in all of the genes listed in Table 1.

In one embodiment the vaccine strain is temperature sensitive.

Attenuated vaccines are generally advantageous because they present all the relevant immunogenic determinants of an infectious agent in its natural form to the host's immune system and the need for relatively small amounts of the immunising agent due to the ability of the agent to multiply in the vaccinated host. Methods for attenuating include passaging a virulent strain multiple times or exposure to irradiation or chemicals. It is assumed that these methods introduce mutations in the genome which render the microorganism less virulent but still capable of replication.

Disadvantages of these approaches are that they introduce random mutations that are not characterised at the molecular level. Also methods for selecting for attenuation, such as by selecting for associated temperature sensitivity are often time consuming, produce false results as a temperature sensitive strain may not be attenuated and an attenuated strain need not be temperature sensitive, and require a great deal of trial and error. Additionally the attenuated strain may undergo further mutation and revert to virulence.

With the aim of providing a live vaccine against mycoplasmal pneumonia the inventors subjected a *Mycoplasma hyopneumoniae* isolate to chemical mutagenesis and selected clones that were temperature sensitive. The inventors freeze dried the live mutant bacteria and found that the bacteria could be reconstituted after a week and remain viable after serial passaging and thus was suitable as a vaccine strain for *Mycoplasma hyopneumoniae*. The vaccine strain and master strain were sequenced and comparison of the sequences identified genes that were mutated in the vaccine, thus allowing genetic characterisation of the attenuated strain.

A second aspect provides an attenuated *Mycoplasma hyopneumoniae* vaccine strain as deposited with the National Measurements Institute (Australia) under accession number NM04/41259, which strain is temperature sensitive and attenuated.

The vaccine strain of the second aspect is shown to confer protective immunity and it shows no reversion to virulence despite serial passaging (data not shown).

A third aspect comprises a method of making the vaccine strain of the first or second aspect, the method comprising subjecting a suitable starting isolate of *Mycoplasma hyopneumoniae* to chemical mutagenesis and selecting mutants which retain viability after serial passaging.

In one embodiment mutants are first selected on the basis of temperature sensitivity.

A fourth aspect provides a vaccine composition comprising the *M. hyopneumoniae* vaccine strain of the first or second aspect and a carrier, optionally an adjuvant, and/or optionally at least one additional infectious agent, which vaccine in an immunizing amount is capable of eliciting protective immunity against a disease caused by *M. hyopneumonia*. The infectious agent may be a virus, a bacterium, a fungus or a parasite, A fifth aspect provides a method for protecting against a disease caused by *Mycoplasma hyopneumoniae* in a porcine animal comprising administering to the porcine animal an immunizing amount of the vaccine composition of the fourth aspect.

A sixth aspect provides the vaccine of the fourth aspect for protecting against a disease caused by *Mycoplasma hyopneumoniae* in a porcine animal.

A seventh aspect provides a method of making a vaccine according to the fourth aspect comprising combining the *Mycoplasma hyopneumoniae* strain of the first or second aspect with a carrier, optionally an adjuvant and/or optionally at least one additional infectious agent. An infectious agent may be a virus, a bacterium, a fungus or a parasite.

An eighth aspect provides the use of the *Mycoplasma hyopneumoniae* vaccine strain of the first or second aspect in the manufacture of a medicament for protecting against disease caused by *Mycoplasma hyopneumoniae* in a porcine animal.

In an embodiment of the fourth to seventh aspects the "disease caused by *Mycoplasma hyopneumoniae*" is enzootic pneumonia or swine mycoplasmal pneumonia.

DETAILED DESCRIPTION

Figure 1:
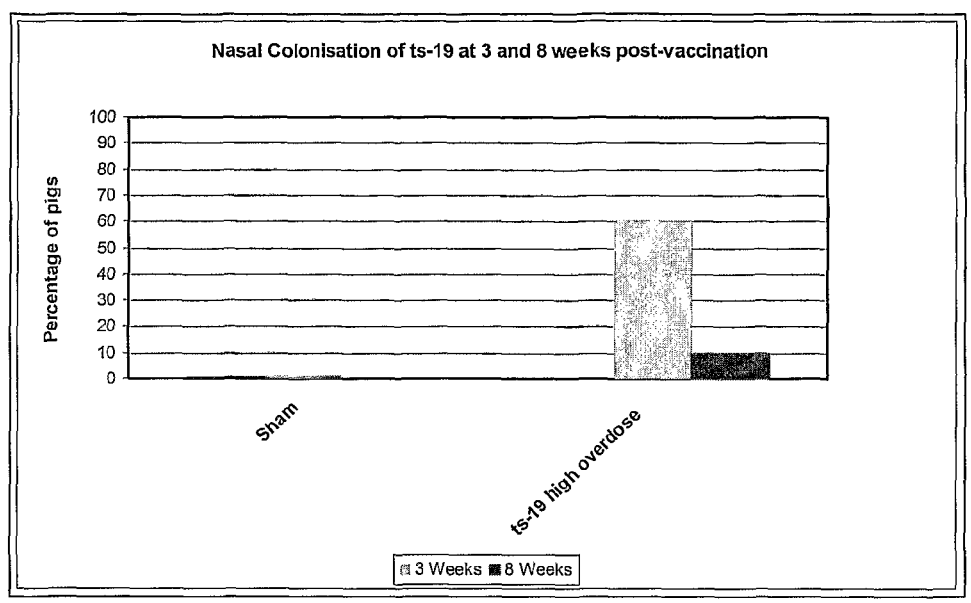
FIG. 1: Nasal colonisation of ts19 vaccine strain in pigs vaccinated at high overdose.

*M. hyopneumoniae* strain "LKR" was originally isolated from an abattoir specimen (Lloyd and Etheridge 1981, J of Comp Path 91:77-83). The organism was reisolated from experimentally infected pigs prior to being passaged about 10 times in acellular medium to reach clonal isolation (CSIRO, Victoria). The clone was then submitted to the University of Adelaide *Mycoplasma* collection, South Australia. The LKR isolate was then obtained by the University of Melbourne, Department of Veterinary Science (*Mycoplasma* Group), where it underwent 3 in vitro passages in modified Friss broth, for storage. The stored vials were designated "LKR P3 29/5/97". This clone represents the parental strain.

LKR P3 29/5/97 was in vitro passaged and subjected to NTG mutagenesis (200 mg/mL) using a method described previously (Nonamura and Imada (1982) Avian Diseases 26:763-775). A temperature sensitive clone ("ts-19") was selected from an agar plate and cultured in 3 mL modified Friss broth. Passage number for this clone was designated "P0" and had subsequently undergone a further four in vitro passages at 1:4 v/v dilution per passage in modified Friss broth. The final passage level was designated "LKR ts-19 P4 MS". LKR ts-19 P4 MS underwent a number of in vitro dilution passages in Modified Friss broth to reach a dilution of $3.2 \times 10^{-21}$. The final mutant clone was designated "LKR ts-19 $3.2 \times 10^{-21}$".

LKR ts-19 $3.2 \times 10^{-21}$ was freeze dried and submitted to Australian Government Analytical Laboratories (Budapest Treaty on the International recognition of the deposit of organisms for the purposes of patent procedure) under the accession number NM04/41259.

Mycoplasmas have a highly reduced genome size which reflects their limited biosynthetic abilities and their parasitic like dependence on their host. In light of the limited redundancy in their genomes, NTG mutagenesis of a particular component of a pathway may have a significant effect on the survival of a *Mycoplasma* cell. NTG mutagenesis results in random mutations (nucleotide transitions, transversions, deletions or insertions) within the genome. This would result in a population of variant genomes each containing either one or more mutations. Presumably many of the variant genomes would not survive due to a critical gene or genes being rendered dysfunctional. If the mutations do not incur a detrimental effect on the organisms ability to grow then those surviving variant organisms can undergo further selection (e.g. temperature selection). In the development of ts19, the selection was based on the ability of the variant strain to grow to high titre at a temperature of 33° C. and the reduced ability to grow at 39.5° C. Based on whole genome sequence comparison between *Mycoplasma hyopneumoniae* vaccine strain ts19 and that of the parent strain (LKR), a number of mutations (nucleotide changes) have been identified within the genome of ts19. These mutations included nucleotide substitutions (transitions and transversions), as well as deletions and insertions.

The mutations were located around the entire genome and include a range of expressed genes as well as hypothetical proteins and non-coding sequences. Table 1 lists the known genes that have been mutated by base substitutions, deletions or insertions. The genes have been categorized according to their main function. Persons skilled in the art would readily appreciate how to detect if a *M. hyo* strain contained a mutation in one of the genes listed in Table 1 by determining if there is a difference between the reference sequence provide (e.g. YP_278901.1) and the sequence of the attenuated strain. Ts19, as deposited as NM04/41259 is an attenuated strain comprising all of the mutations listed in Table 1.

In one embodiment the attenuated strain comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or all of the mutations listed in Table 1. In one embodiment the attenuated strain comprises a mutation in one or each of the virulence factors, and/or one or each of the genes involved in carbohydrate metabolism, and/or the gene involved in phospholipid metabolism, and/or the gene involved in co-factor metabolism, and/or one or each of the genes involved in transcription or translation, and/or one or each of the genes involved in membrane transport, and/or one or each of the genes involved in DNA replication, repair or metabolism and/or the transposase gene listed in Table 1.

In one embodiment the attenuated strain comprises a mutation in each of the virulence factors.

TABLE 1

| Attenuating Mutations within genes of *M. hyopneumoniae* vaccine strain ts19. | |
|---|---|
| Virulence factors: | |
| Putative outer membrane protein P95 | YP_278901.1 |
| Putative lipoprotein (MHJ_0213) | YP_279015.1 |
| Putative lipoprotein (MHJ_0362) | YP_279161.1 |
| Putative P216 surface protein | YP_279290.1 |
| Putative adhesion like-protein P146 | YP_279457.1 |
| Carbohydrate Metabolism: | |
| Triosephosphate isomerase | YP_278904.1 |
| Transketolase | YP_279223.1 |
| Putative PTS system N-acetylglucosamine-specific II ABC component | YP_279370.1 |
| Phospholipid Metabolism: | |
| CDP-diacylglycerol-glycerol-3-phosphate-3-phosphatidyal transferase | YP_279075.1 |
| Co-factors Metabolism: | |
| Nicotinate phosphoribosyltransferase | YP_279204.1 |
| Transcription/translation: | |
| GidA gene [tRNA uridine 5-carboxymethylaminomethyl modification enzyme | YP_278808.1 |
| 50S Ribosomal protein L3 | YP_278992.1 |

TABLE 1-continued

Attenuating Mutations within genes of
M. hyopneumoniae vaccine strain ts19.

| | |
|---|---|
| Leucyl-tRNA synthetase | YP_279441.1 |
| Isoleucyl tRNA synthetase | YP_278833.1 |
| Membrane Transport: | |
| Putative ABC transporter permease protein | YP_279164.2 |
| Putative ABC transporter ATP binding | YP_278823.1 |
| Putative chromate transport protein | YP_278943.1 |
| Putative ABC transporter ATP binding and permease protein | YP_278958.1 |
| Putative inner membrane protein translocase component YidC | YP_279468.1 |
| Putative ABC transport system permease protein p69-like | YP_279157.1 |
| Putative ABC transporter permease protein | YP_279176.1 |
| Putative ABC transporter ATP-binding-Pr1 | YP_279419.1 |
| DNA replication/repair/metabolism | |
| DNA topoisomerase I | YP_279077.1 |
| Uracil-DNA glycosylase | YP_278929.1 |
| GTPase ObgE | YP_278842.1 |
| DNA polymerase IV | YP_278846.1 |
| Ribonucleotide-disulphate reductase subunit alpha | YP_279017.1 |
| Thymidylate kinase | YP_279053.1 |
| DNA polymerase III subunit delta | YP_279054.1 |
| DNA ligase | YP_279060.1 |
| DNA gyrase subunit A | YP_279326.1 |
| ribonuclease HII | YP_279388.1 |
| Inorganic pyrophosphatase | YP_279400.1 |
| Excinuclease ABC subunit C | YP_278867.1 |
| Transposase | |
| putative ISMHp1 transposase | YP_279110.1 |

YP_number indicates NCBI Reference Sequence

The bacterial strain described herein is a live temperature sensitive and attenuated strain and can be used in a live vaccine.

A live, attenuated strain is a live bacterial strain that has been cultivated under conditions that reduce or "attenuate" their virulent properties. Live vaccines typically provoke a more durable immunological response than inactivated or killed microorganisms.

The vaccine strain according to the first aspect may be produced by chemical mutation of a *Mycoplasma hyopneumoniae* isolate. The chemical mutation particularly comprises mutagenesis by treatment with N-Methyl-N'-nitro-N-nitrosoguanidine (NTG) (Nonamura and Imada (1982), Avian Diseases 26; 763-775). Temperature sensitive mutant bacteria may be selected for their ability to grow at a permissive temperature (33° C.) and not able to grow at a non-permissive temperature (39.5° C.). For use in a vaccine the temperature sensitive mutants undergo serial passaging and dilution.

The *Mycoplasma* bacterial vaccine strain according to the first aspect is viable (or live). Viability means in general "capacity for survival" and is more specifically used to mean a capacity for living, developing, or germinating under favorable conditions. A bacterial cell is viable if it is capable of growing in either a suitable broth or agar media.

The bacterial strain deposited under the Budapest Treaty as NM 04/41259 was produced by in vitro passaging three times (3×) at (1:4 v/v in modified Friss broth) of Australian *Mycoplasma hyopneumonia* isolate LKR (obtained from the University of Adelaide *Mycoplasma* collection by the University of Melbourne *Mycoplasma* Group) to produce LKR P3. The LKR P3 isolate was then subjected to NTG mutagenesis. Mutagenized LKR P3 was grown on agar at 33° C. (a permissive temperature) and at 39.5° C. (non-permissive temperature). Mutant clones that grew at 33° C. but did not grow at 39.5° C. were selected. The selected clones underwent several rounds of in vitro passaging and serial dilution. At the final round of passaging, a selected clone (ts19) was deposited under the Budapest Treaty at the National Measurements Institute (then called Australian Government Analytical Laboratories) as a freeze dried culture. The samples were reconstituted after one week of storage and were found to be viable.

The term "in vitro serial passaging" refers to the practice of repeated passage of bacteria in media. It involves inoculating a broth medium with a live bacterial culture which is then given some time to incubate at the appropriate temperature. A portion of the incubated culture is then used to inoculate a fresh sterile culture which in turn is given some time to incubate. The cycle continues to achieve the desired number of passages. Each round of growth and re-inoculation is referred to as a single passage.

The third aspect provides a vaccine comprising the bacterial strain of the first aspect and a carrier such as *M. hyopneumoniae* growth media, sterile water or sterile isotonic saline.

A vaccine is a biological preparation that establishes or improves immunity to a particular disease. Vaccines can be prophylactic (e.g. to prevent or ameliorate the effects of a future infection by the pathogen), or therapeutic (e.g. to treat the infection). The vaccine of the second aspect is prophylactic for a disease caused by *Mycoplasma hyopneumonia*.

The appropriate carrier will be evident to those skilled in the art and will depend in large part upon the route of administration. The vaccine may further comprise one or more additional ingredients including, but not limited to, suspending, stabilizing, or dispersing agents.

Still additional components that may be present in the vaccine are adjuvants, preservatives, chemical stabilizers, or other antigenic proteins. Typically, stabilizers, adjuvants, and preservatives are optimized to determine the best formulation for efficacy in the target animal. Suitable exemplary preservatives include chlorobutanol potassium sorbate, sorbic acid, sulfur dioxide, propyl gallate, the parabens, ethyl vanillin, glycerin, phenol, and parachlorophenol. Suitable stabilizing ingredients which may be used include, for example, casamino acids, sucrose, gelatin, phenol red, N—Z amine, monopotassium diphosphate, lactose, lactalbumin hydrolysate, and dried milk. A conventional adjuvant is used to attract leukocytes or enhance an immune response. Such adjuvants include, among others, MPL™ (3-O-deacylated monophosphoryl lipid A; RIBI ImmunoChem Research, Inc., Hamilton, Mont.), mineral oil and water, aluminum hydroxide, Amphigen, Avridine, L121/squalene, D-lactide-polylactide/glycoside, pluronic plyois, muramyl dipeptide, killed *Bordetella*, saponins, such as Quil A or Stimulon™ QS-21 (Aquila Biopharmaceuticals, Inc., Framingham, Mass.) and cholera toxin (either in a wild-type or mutant form, e.g., wherein the glutamic acid at amino acid position 29 is replaced by another amino acid, preferably a histidine, in accordance with International Patent Application No. PCT/US99/22520).

In one embodiment, the vaccine, if injected has little or no adverse or undesired reaction at the site of the injection, e.g., skin irritation, swelling, rash, necrosis, skin sensitization.

The invention in a fourth aspect relates to protecting against disease caused by *Mycoplasma hyopneumoniae*. The vaccine of the third aspect is prophylactic for a disease caused by *Mycoplasma hyopneumoniae*.

"Prophylaxis" or "prophylactic" or "preventative" therapy or "protecting against" as referred to herein includes keeping the infection from occurring or to hinder or defend from or protect from the occurrence or severity of a disease caused by *Mycoplasma hyopneumoniae*, including preventing, protecting or lessening the severity of a symptom or feature of the disease in a subject that may be predisposed to the disease, but has not yet been diagnosed as having it. It also includes reducing the period of infection or incidence of symptoms and reducing the size of any lesions.

"Prophylaxis" as used herein covers total prevention of the disease or a reduction in the extent or symptoms of the disease. It also refers to the reduction or inhibition of transmission of *Mycoplasma hyopnemonia* or preventing the bacteria establishing in the host or protection against secondary infection with other *Mycoplasma hyopnemonia* strains or other infectious agents.

The vaccine of the third aspect may be prepared for administration to pigs in the form of for example, liquids, powders, aerosols, tablets, capsules, enteric coated tablets or capsules, or suppositories. Routes of administration include, without limitation, parenteral administration, intraperitoneal administration, intravenous administration, intramuscular administration, subcutaneous administration, intradermal administration, oral administration, topical administration, intranasal administration, intra-pulmonary administration, rectal administration, vaginal administration, and the like.

In a preferred embodiment the vaccine is formulated for administration to the respiratory tract, for example by intranasal administration, aerosol administration or administration by inhalation by the mouth or nose. This route of administration is preferred because the nature of protective immunity for *M. hyopneumoniae* may be local (pulmonary) immunity and cell-mediated immunity in preventing the disease rather than from circulating antibodies. Presentation of the vaccine to the respiratory tract may stimulate a local immune response. Therefore localised administration of the vaccine may be more effective. Furthermore by administering the vaccine in an enclosed barn or space (coarse spray mass administration) and allowing the pigs to inhale it, reduces the labour involved in vaccinating large numbers of animals. Aerosol vaccination (or spray vaccination) is currently used on a commercial basis to effectively vaccinate poultry against certain diseases and has been shown in our examples to be suitable for vaccinating pigs.

Intranasal administration covers any administration via the nasal passages or snout. The vaccine may be applied to the nasal cavity as a solution, suspension or dry powder. Solutions and suspensions may be administered intranasally using, for example, a pipette, a dropper or a spray, optionally an aerosol spray. Dry powders may be administered intranasally by inhalation.

Aerosol administration refers to administration of the vaccine in as a suspension of fine solid particles or liquid droplets in a gas.

Inhalation (also known as inspiration) is the movement of air from the external environment, through the air ways, and into the alveoli in the lungs.

An effective dose of vaccine to be employed therapeutically will depend, for example, upon the therapeutic objectives, the route of administration, and the condition of the pig.

Dosage levels for the vaccine will usually be of the order of about $10^4$ to $10^8$ colour changing units (CCU) per mL per dose, and preferably about $10^5$ to $10^7$ CCU per mL per dose.

It will be understood, however, that the specific dose level for any particular porcine animal will depend upon a variety of factors including the activity of the specific compound employed, the age, body weight, general health, sex, diet, time of administration and route of administration.

Selection and upward or downward adjustment of the effective dose is within the skill of the art.

In a preferred embodiment the vaccine is administered intranasally, by aerosol or by inhalation.

The terms "pig" and "swine" are used herein interchangeably and refer to piglets, sows, gilts, barrows, boars and members of the Suidae family.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

It must also be noted that, as used in the subject specification, the singular forms "a", "an" and "the" include plural aspects unless the context clearly dictates otherwise.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The invention is now further described in detail by reference to the following example. The example is provided for purposes of illustration only, and is not intended to be limiting unless otherwise specified. Thus, the invention encompasses any and all variations which become evident as a result of the teaching provided herein.

Example 1

Preparation of Vaccine Strain

Australian *Mycoplasma hyopneumoniae* isolate LKR is an abattoir specimen of pig lung exhibiting typical enzootic pneumonia disease (Lloyd and Etheridge (1981), J. Comp. Path. 91:77-83). The isolate was cultured and stored at the *Mycoplasma* reference culture collection at the University of Adelaide, South Australia. A culture of this isolate was subsequently obtained by the *Mycoplasma* group at the University of Melbourne, Victoria.

The culture was in vitro passaged three times before being subjected to mutagenesis using N-Methyl-N'-nitro-N-nitrosoguanidine (NTG) at 200 mg/mL using a method described previously (Nonamura and Imada (1982) Avian Diseases 26:763-775). Briefly, a culture of *M. hyopneumoniae* strain LKR was growth to late log phase and pelleted by centrifugation. The cells were washed in phosphate buffered saline (PBS) and exposed to NTG. The cells were pelleted and resuspended in modified Friis media (Friis, N. F. 1975) and incubated at 33° C. for 4 h. The culture was then passed through a 0.45 μm filter, appropriate dilutions made and aliquots placed onto agar plates and incubated at 33° C. Colonies that had grown were cloned into 3 mL of broth and incubated at 33° C. Ampoules of the clones were stored at −70° C. and the temperature sensitivity of each clone determined.

The temperature sensitivity of ts19 was determined by performing a duplicate titration and incubation at 33° C. and 39.5° C. The titre is typically >$1\times10^8$ CCU/mL at 33° C. and <$1\times10^2$ CCU/mL at 39.5° C.

The ts19 strain was deposited under the Budapest Treaty as NM 04/41259.

The ts19 strain and the LKR strain were sequenced using standard techniques, thus allowing the attenuated strain to be genetically characterised. The ts19 strain was found to contain a number of genetic mutations compared to its master strain and the genes containing these mutations are identified in Table 1.

Example 2

Vaccine Preparation

To prepare a vaccine, a culture of ts19 was grown at 33° C. in modified Friis media containing phenol red (pH indicator) until an acid colour change was observed. Vaccine was titrated in modified Friis media using a 96 well microtitre plate. A series of ten-fold dilutions were performed across the first 10 out of the 12 columns of the microtitre plate. The last two lanes remained un-inoculated and served as a media only (negative) control. Up to six microtitre plates were used at each titration.

After incubation up to 3 weeks the plates were scored for colour change and the average titre determined using the most probably number (MPN). The final average titre is expressed as colour changing units (CCU) per mL.

The ts19 vaccine culture was kept at long term storage as a "wet frozen" format at −70° C. to −80° C. Alternatively, the ts19 vaccine culture was lyophilized (freeze dried) and kept at long term storage at −20° C.

Example 3

Vaccine Safety and Colonisation Study

A study was conducted in order to evaluate the safety profile of the ts19 vaccine strain. The study design entailed the use of 6-week-old pigs obtained from a *Mycoplasma* free pig herd. The study was conducted under PC2 biosecurity level at the CSIRO (Commonwealth Serum Industry Research Organisation), Werribee, Victoria, Australia. A total of 20 pigs were randomly assigned to two groups of 10 pigs each (see Table 2).

TABLE 2

Safety study on ts19 vaccine strain.

| Group | Purpose | Number of pigs treated with *M. hyopneumoniae* media on first day of the trial | Number of pigs Vaccinated with ts-19 (CCU/dose) on first day of the trial | Total number of pigs per group |
|---|---|---|---|---|
| 1 | Sham-vaccinated (negative control) | 10 | — | 10 |
| 2 | Safety (High Overdose) | — | 10 | 10 |
| Total | | | | 20 |

The vaccine was delivered via intranasal route thereby only testing safety for mucosal presentation of the vaccine. Group 1 (unvaccinated control) and Group 2 (high overdose vaccinated pigs) were held for 59 days for clinical observation (Table 2).

All pigs in this safety study were monitored twice daily for rectal body temperature starting one day pre-vaccination as well as four days post-vaccination. All pigs were also monitored for respiratory signs including coughing, sneezing, dyspnoea and tachypnoea. All pigs were evaluated for microscopic and macroscopic lung lesions. Macroscopic lung lesions were scored using the Hannan et al, 1982 method. In addition, swab samples were taken of nasal, lung and trachea for purposes of PCR analysis.

Pigs from each group were also tested 3 weeks post vaccination for the presence of *M. hyopneumoniae* in their nasal cavities using a PCR technique. Finally, pigs were monitored for weight gain over the study period. The results showed that no clinical signs were observed in any of the pigs. There was no significant increase in temperature detected between vaccinated groups and the unvaccinated control group. Furthermore, no significant differences in body weight gain were seen between the vaccinated and the unvaccinated control groups. At necropsy, two pigs out ten from the high overdose group each had a small macroscopic lesion typical of enzootic pneumoniae. No additional lesions were observed by microscopic analysis of lung tissue. Overall, the temperature sensitive vaccine strain ts19 showed to be safe even at a high overdose.

Figure 2:
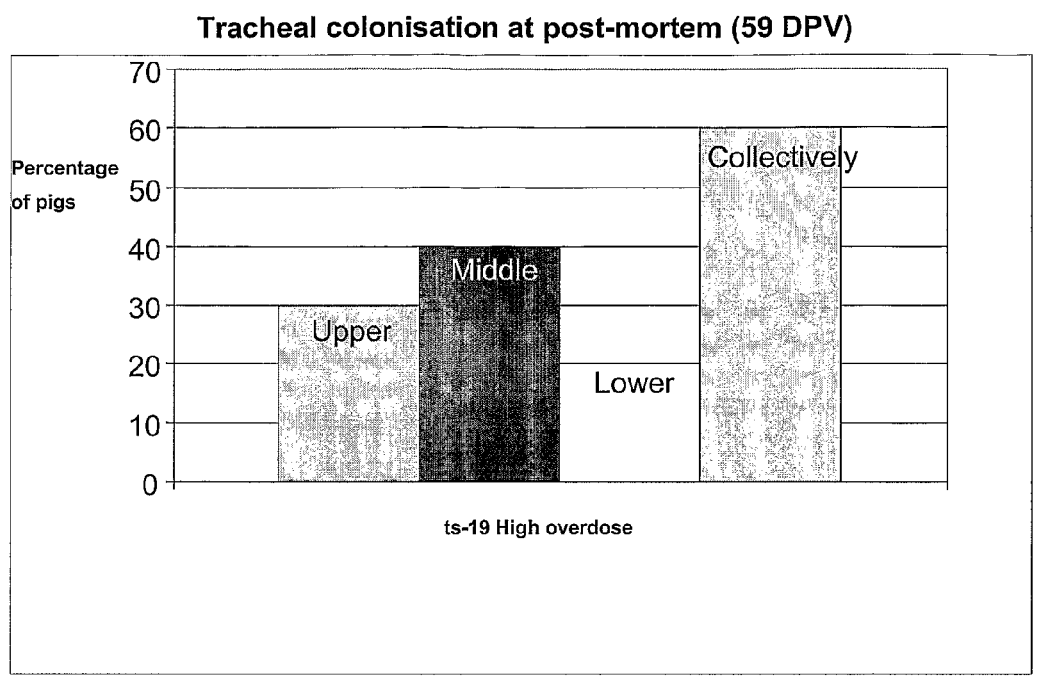
FIG. 2: Tracheal colonisation at 59 days post vaccination (DPV) in pigs vaccinated at high overdose with ts19 vaccine.

PCR analysis (using primers specific for *M. hyopneumoniae*) showed presence of *M. hyopneumoniae* in the nasal passages of vaccinated pigs at 3 weeks and 8 weeks post vaccination (see FIG. 1). *M. hyopnuemoniae* colonisation studies using PCR analysis also showed presence of *M. hyopnuemoniae* in the trachea (either at the upper, middle and lower regions) and collectively in at least 60% of the trachea of vaccinated pigs (see FIG. 2). These results indicate colonisation of the ts19 vaccine strain in the nasal and tracheal passages.

Example 4

Vaccine Efficacy Study Challenge Model—Show Protection

A study was conducted in order to evaluate the efficacy of the ts19 vaccine strain. The study design entailed use of 6-week-old pigs obtained from a *Mycoplasma* free pig herd. The study was conducted under PC2 biosecurity level at the CSIRO (Commonwealth Serum Industry Research Organisation), Werribee, Victoria, Australia. A total of 56 pigs were randomly assigned to three groups of 12 pigs for each vaccinated group and 10 pigs for each of the control groups (see Table 3).

TABLE 3

Efficacy study on ts19 vaccine

| Group | Purpose | Number of pigs treated with *M. hyopneumoniae* media on day one of the trial | Vaccination with ts-19 on day one of the trial (CCU/dose) | Number of pigs challenged with Australian field isolate on day 22 of the trial | Total number of pigs per group |
|---|---|---|---|---|---|
| 1 | Sham vaccinated (negative control) | 10 | — | — | 10 |

TABLE 3-continued

Efficacy study on ts19 vaccine

| Group | Purpose | Number of pigs treated with M. hyopneumoniae media on day one of the trial | Vaccination with ts-19 on day one of the trial (CCU/dose) | Number of pigs challenged with Australian field isolate on day 22 of the trial | Total number of pigs per group |
|---|---|---|---|---|---|
| 2 | Efficacy | — | $10^6$ | 12 | 12 |
| 3 | Efficacy | — | $10^7$ | 12 | 12 |
| 4 | Efficacy | — | $10^8$ | 12 | 12 |
| 5 | Non-vaccinated. (Positive control) | — | — | 10 | 10 |
| Total | | | | | 56 |

The vaccine was delivered via intranasal route thereby only testing efficacy for mucosal presentation of the vaccine. All groups except the unvaccinated, unchallenged negative group were challenged at 22 days post vaccination by intranasal administration of an Australian field isolate of M. hyopneumoniae. Post-mortem examinations were conducted over 3 days (days 57, 58 and 59 post vaccination). Throughout the study all groups were monitored daily for clinical signs including coughing, sneezing, dyspnoea and tachypnoea. Body weight measurements were taken at the start and at the end of the study.

At 22 days post vaccination (and prior to challenge) nasal swabs were taken for PCR analysis to determine presence of M. hyopneumoniae from each group.

Figure 3:
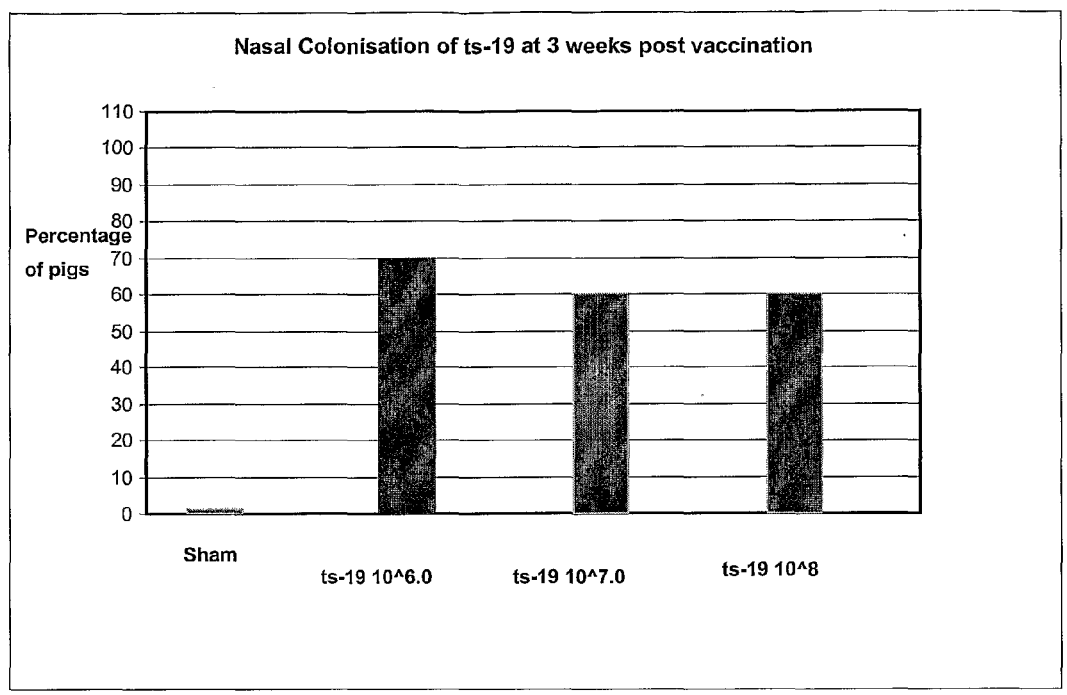
FIG. 3: Nasal colonisation in pigs vaccinated with ts19 vaccine strain at various doses.

The results showed that no clinical signs and no significant difference in body weight gain were observed in all groups tested. Nasal swab analysis showed presence of M. hyopneumoniae at 22 days post vaccination in 60-70% of vaccinated pigs pre-challenge (see FIG. 3). All sham-vaccinated control pigs were negative for M. hyopneumoniae by PCR analysis. At necropsy, macroscopic lesion analysis (Hannan et al., 1982) indicated the absence of lesions in the sham-vaccinated control group as well as the groups vaccinated at $10^6$ and $10^7$ CCU/mL/dose. One out of 10 pigs vaccinated at a $10^8$ CCU/mL/dose showed presence of a small macroscopic lesion. However, 4 out of 10 pigs which were unvaccinated but challenged showed clinical signs of coughing and sneezing. At necropsy, examination of the lungs from the four pigs showed macroscopic lung lesions typical of M. hyopneumoniae infection.

Overall, the temperature sensitive vaccine strain ts19 showed to be efficacious in protecting against M. hyopneumoniae infection.

Example 5

Vaccine Efficacy at Different Doses and Comparison with a Commercial Killed Vaccine A study was conducted in order to evaluate the efficacy of the ts19 vaccine strain at four different doses. The study design entailed use of 3-4 week-old spf pigs. The study was conducted in a PC2 facility at Centro de Nacional de Servicios de Diagnostico en Salud Animal (CENASA)—a government testing facility in Tecamac, Mexico. A total of 70 pigs were randomly assigned to seven groups each containing 10 pigs (Table 4).

TABLE 4

Minimum protective dose and comparative efficacy study

| Group | Purpose | Vaccine dose ccu/mL/dose | Number of pigs vaccinated | Number of pigs challenged | Total number of pigs per group |
|---|---|---|---|---|---|
| 1 | Sham cont. | NA | 0 | 0 | 10 |
| 2 | ts19 [a] | $10^{3.0}$ | 10 | 10 | 10 |
| 3 | ts19 [a] | $10^{4.0}$ | 10 | 10 | 10 |
| 4 | ts19 [a] | $10^{5.0}$ | 10 | 10 | 10 |
| 5 | ts19 [a] | $10^{6.0}$ | 10 | 10 | 10 |
| 6 | Commerical inactivated [b] | 2 mL | 10 | 10 | 10 |
| 7 | Positive control | NA | 0 | 10 | 10 |
| Total | NA | NA | 50 | 60 | 70 |

[a] Vaccine was delivered by intranasal spray
[b] Vaccine was delivered by intramuscular administration Four different doses of ts19 vaccine ($10^3$, $10^4$, $10^5$, $10^6$ CCU/mL) were delivered to four separate groups of pigs by intranasal route. A fifth group received 2 mL of a commercial inactivated vaccine delivered by intramuscular route. Positive (unvaccinated but challenged) and negative (unvaccinated, unchallenged) groups were also included in this study. All groups except the negative control group were challenged at two time points. The first challenge was conducted at 22 days post vaccination by intranasal administration using a US isolate of M. hyopneumoniae (IOWA strain 194). The second challenge was conducted at 84 days post vaccination using the same challenge strain. Throughout the study all groups were monitored daily for clinical signs including coughing, sneezing, dyspnoea and tachypnoea. Body weight measurements were taken at the start and at the end of the study.

Figure 4:
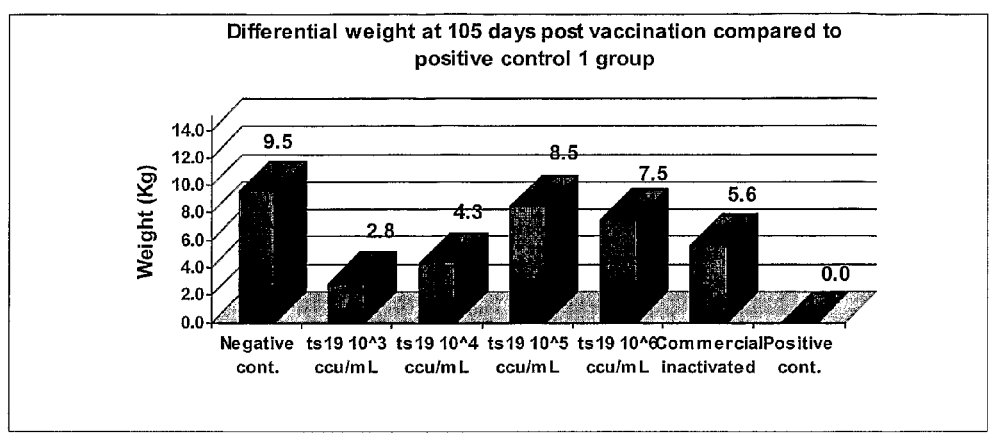
FIG. 4: Differential total body weights over the study period (105 days).
Figure 5:
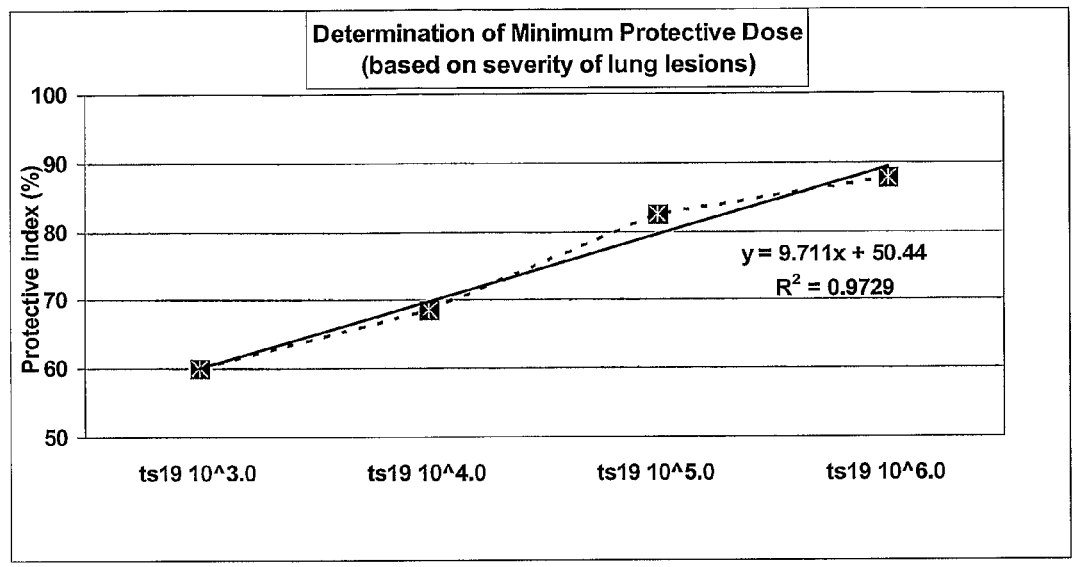
FIG. 5: Minimum Protective Dose determination for ts19.
Figure 6:
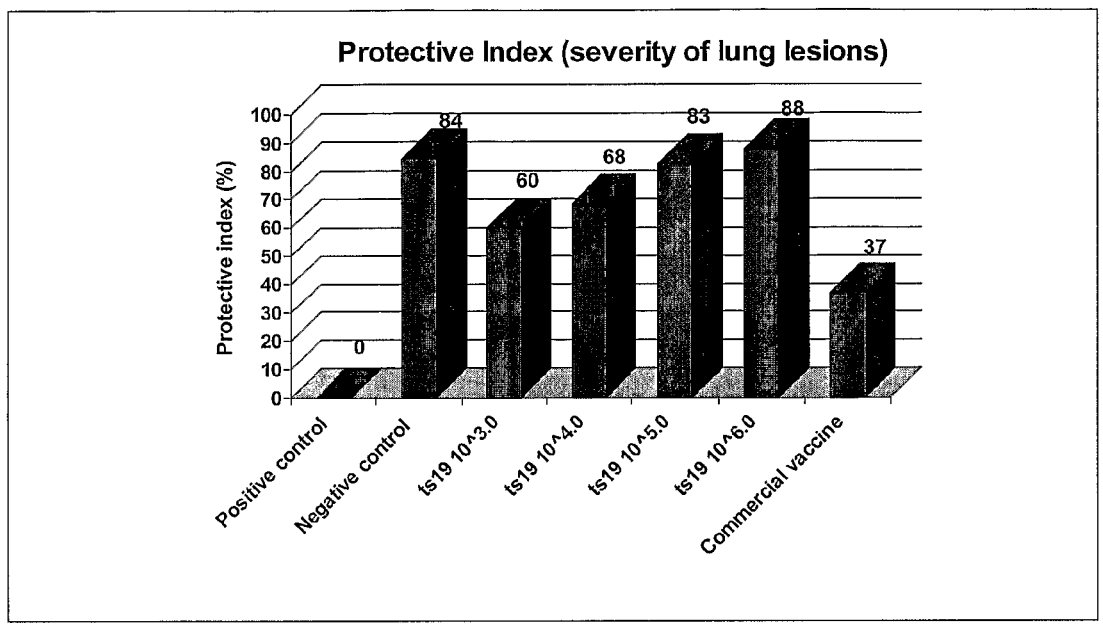
FIG. 6: Protective index of ts19 and commercial vaccine based on reduction in the severity of lung lesions.

The results showed that no clinical signs over the entire testing period of 105 days. Analysis of variance for weight performance between the positive control group and each of the vaccinated groups indicated that ts19 at doses of $10^5$ and $10^6$ CCU/mL showed significant gain in body weight compared with the positive control group (FIG. 4). The group vaccinated with the commercial vaccine did not show any significant difference in weight gain when compared to the positive control group (FIG. 4, Table 5). At necropsy, macroscopic lesion analysis was performed for each group. The criterion for determination of the minimum protective dose was based on a protective index of ≧70% with respect to reduction in severity of lung lesions. The minimum protective dose for ts19 was determined to be $10^4$ CCU/mL since a protective index of 70% was achieved at this dose with respect to the reduction in the severity of lung lesions (FIG. 5). Higher doses of ts19 ($10^5$ and $10^6$ CCU/mL) were also tested and found to provide PIs of 83% and 88% respectively relative to reduction in severity of lung lesions (FIG. 6). The commercial inactivated vaccine attained a PI of only 37% which is well below the lowest dose of ts19 used ($10^3$ CCU/mL which attained a PI of 60%).

TABLE 5

Analysis of Variance of the average weight gain of vaccinated groups compared with the positive control group on DPV-104/105

| Group | Treatment | Analysis of Variance (P) compared to the positive control |
|---|---|---|
| 1 | Negative control | 0.001 |
| 2 | ts19 $10^{3.0}$ | 0.394 |
| 3 | ts19 $10^{4.0}$ | 0.175 |
| 4 | ts19 $10^{5.0}$ | 0.033 |
| 5 | ts19 $10^{6.0}$ | 0.004 |
| 6 | Commercial vaccine | 0.315 |
| 7 | Positive control | NA | ts19 doses (ccu/mL). No significant difference ($P > 0.05$), significant difference ($P < 0.05$).

The invention claimed is:

1. A vaccine composition comprising an adjuvant together with the *Mycoplasma hyopneumoniae* strain deposited with the National Measurements Institute, Australia under accession number NM04/41259, which strain is temperature sensitive and attenuated, prepared by subjecting a suitable starting strain of *Mycoplasma hyopneumoniae* to chemical mutagenesis and selecting a temperature sensitive mutant that remains viable after a serial in vitro passaging, which vaccine in an immunizing amount is capable of eliciting protective immunity against a disease caused by *Mycoplasma hyopneumoniae*.

2. The vaccine composition of claim 1, wherein the *Mycoplasma hyopneumoniae* vaccine strain further comprises a mutation in at least one gene selected from Putative outer membrane protein P95, Putative lipoprotein MHJ_0213, Putative lipoprotein MHJ_0362, Putative P216 surface protein, Putative adhesion like-protein PI46, Triosephosphate isomerase, Transketolase, Putative PTS system N-acetylglucosamine-specific II ABC component, CDP-diacylglycerol-glycerol-3-phosphate-3-phosphatidyal transferase, Nicotinate phosphoribosyltransferase, GidA gene [tRNA uridine 5-carboxymethylaminomethyl modification enzyme, 50S Ribosomal protein L3, Leucyl-tRNA synthetase, Isoleucyl tRNA synthetase, Putative ABC transporter permease protein, Putative ABC transporter ATP binding, Putative chromate transport protein, Putative ABC transporter ATP binding and permease protein, Putative inner membrane protein translocase component YidC, Putative ABC transport system permease protein p69-like, Putative ABC transporter permease protein, Putative ABC transporter ATP-binding-PrI, DNA topoisomerase I, Uracil-DNA glycosylase, GTPase ObgE, DNA polymerase IV, Ribonucleotide-disulphate reductase subunit alpha, Thymidylate kinase, DNA polymerase III subunit delta, DNA ligase, DNA gyrase subunit A, ribonuclease HII, Inorganic pyrophosphatase, Excinuclease ABC subunit C and putative ISMHpl transposase.

3. The vaccine composition of claim 1, wherein the *Mycoplasma hyopneumoniae* vaccine strain further comprises mutations in all the following genes Putative outer membrane protein P95, Putative lipoprotein MHJ_0213, Putative lipoprotein MHJ_0362, Putative P216 surface protein, Putative adhesion like-protein PI46 Triosephosphate isomerase, Transketolase, Putative PTS system N-acetylglucosamine-specific II ABC component, CDP-diacylglycerol-glycerol-3-phosphate-3-phosphatidyal transferase, Nicotinate phosphoribosyltransferase, GidA gene [tRNA uridine 5-carboxymethylaminomethyl modification enzyme, 50S Ribosomal protein L3, Leucyl-tRNA synthetase, Isoleucyl tRNA synthetase, Putative ABC transporter permease protein, Putative ABC transporter ATP binding, Putative chromate transport protein, Putative ABC transporter ATP binding and permease protein, Putative inner membrane protein translocase component YidC, Putative ABC transport system permease protein p69-like, Putative ABC transporter permease protein, Putative ABC transporter ATP-binding-PrI, DNA topoisomerase I, Uracil-DNA glycosylase, GTPase ObgE, DNA polymerase IV, Ribonucleotide-disulphate reductase subunit alpha, Thymidylate kinase, DNA polymerase III subunit delta, DNA ligase, DNA gyrase subunit A, ribonuclease HII, Inorganic pyrophosphatase, Excinuclease ABC subunit C and putative ISMHpl transposase.

4. A *Mycoplasma hyopneumoniae* vaccine strain deposited with the National Measurements Institute (Australia) under accession number NM04/41259, which strain is temperature sensitive and attenuated.

5. A vaccine composition comprising the *Mycoplasma hyopneumoniae* strain of claim 4 which vaccine in an immunizing amount is capable of eliciting protective immunity against a disease caused by *Mycoplasma hyopneumoniae*.

6. The vaccine composition of claim 5, further comprising an infectious agent selected from the group consisting of a virus, a bacterium, a fungus or a parasite.

7. The vaccine composition of claim 5 formulated for administration to the respiratory tract.

8. The vaccine composition of claim 5 in aerosol formulation.

9. The vaccine of claim 5, wherein the vaccine in present in an immunizing amount effective against enzootic pneumonia or swine mycoplasmal pneumonia.

10. A vaccine composition comprising a carrier together with the *Mycoplasma hyopneumoniae* strain of claim 4, which vaccine in an immunizing amount is capable of eliciting protective immunity against a disease caused by *Mycoplasma hyopneumoniae*.

11. The vaccine composition of claim 10, further comprising an infectious agent selected from the group consisting of a virus, a bacterium, a fungus or a parasite.

12. The vaccine composition of claim 10 formulated for administration to the respiratory tract.

13. The vaccine composition of claim 10 in aerosol formulation.

14. A method of making the vaccine comprising combining the *Mycoplasma hyopneumoniae* strain of claim 4 with a carrier, an adjuvant or an infectious agent.

15. The *Mycoplasma hyopneumoniae* vaccine strain of claim 4, further comprising a mutation in at least one gene selected from Putative outer membrane protein P95, Putative lipoprotein MHJ_0213, Putative lipoprotein MHJ_0362, Putative P216 surface protein, Putative adhesion like-protein PI46, Triosephosphate isomerase, Transketolase, Putative PTS system N-acetylglucosamine-specific II ABC component, CDP-diacylglycerol-glycerol-3-phosphate-3-phosphatidyal transferase, Nicotinate phosphoribosyltransferase, GidA gene [tRNA uridine 5-carboxymethylaminomethyl modification enzyme, 50S Ribosomal protein L3, Leucyl-tRNA synthetase, Isoleucyl tRNA synthetase, Putative ABC transporter permease protein, Putative ABC transporter ATP binding, Putative chromate transport protein, Putative ABC transporter ATP binding and permease protein, Putative inner membrane protein translocase component YidC, Putative ABC transport system permease protein p69-like, Putative ABC transporter permease protein, Putative ABC transporter ATP-binding-Prl, DNA topoisomerase I, Uracil-DNA glycosylase, GTPase ObgE, DNA polymerase IV, Ribonucleotide-disulphate reductase subunit alpha, Thymidylate kinase, DNA polymerase III subunit delta, DNA ligase, DNA gyrase subunit A, ribonuclease HII, Inorganic pyrophosphatase, Excinuclease ABC subunit C and putative ISMHp1 transposase.

16. The *Mycoplasma hyopneumoniae* vaccine strain of claim 4, further comprising mutations in all the following genes Putative outer membrane protein P95, Putative lipoprotein MHJ_0213, Putative lipoprotein MHJ_0362, Putative P216 surface protein, Putative adhesion like-protein P146, Triosephosphate isomerase, Transketolase, Putative PTS system N-acetylglucosamine-specific II ABC component, CDP-diacylglycerol-glycerol-3-phosphate-3-phosphatidyal transferase, Nicotinate phosphoribosyltransferase, GidA gene [tRNA uridine 5-carboxymethylaminomethyl modification enzyme, 50S Ribosomal protein L3, Leucyl-tRNA synthetase, Isoleucyl tRNA synthetase, Putative ABC transporter permease protein, Putative ABC transporter ATP binding, Putative chromate transport protein, Putative ABC transporter ATP binding and permease protein, Putative inner membrane protein translocase component YidC, Putative ABC transport system permease protein p69-like, Putative ABC transporter permease protein, Putative ABC transporter ATP-binding-Prl, DNA topoisomerase I, Uracil-DNA glycosylase, GTPase ObgE, DNA polymerase IV, Ribonucleotide-disulphate reductase subunit alpha, Thymidylate kinase, DNA polymerase III subunit delta, DNA ligase, DNA gyrase subunit A, ribonuclease HII, Inorganic pyrophosphatase, Excinuclease ABC subunit C and putative ISMHp1 transposase.

17. A method for reducing the likelihood of disease caused by *Mycoplasma hyopneumoniae* in a porcine animal comprising administering to the porcine animal an immunizing amount of the vaccine composition of claim 5.

18. The method of claim 17, in which the vaccine is administered to the respiratory tract.

19. The method of claim 17, in which the vaccine is administered by inhalation, intranasally or via an aerosol.

\* \* \* \* \*